Figure 1:
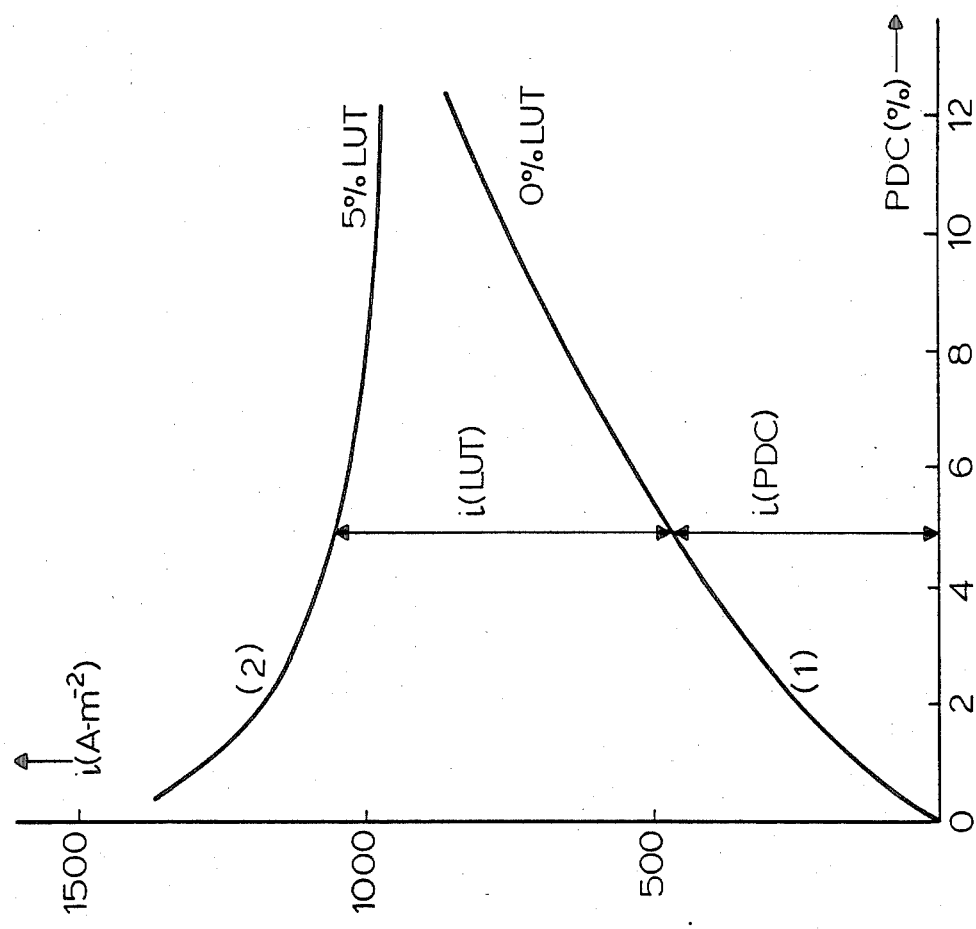

United States Patent [19]

Alfenaar et al.

[11] Patent Number: 4,693,793

[45] Date of Patent: Sep. 15, 1987

[54] PROCESS FOR THE ELECTROCHEMICAL OXIDATION OF ALKYLPYRIDINES

[75] Inventors: Marinus Alfenaar, Schinnen; Franciscus van den Brink, Geldrop; Rudolf van Hardeveld, Geleen, all of Netherlands

[73] Assignee: Stamicarbon B.V., Geleen, Netherlands

[21] Appl. No.: 905,398

[22] Filed: Sep. 10, 1986

[30] Foreign Application Priority Data

Sep. 11, 1985 [NL] Netherlands ............. 8502485
Sep. 11, 1985 [NL] Netherlands ............. 8502486

[51] Int. Cl.4 ............................................. C25B 3/02
[52] U.S. Cl. ...................................................... 204/78
[58] Field of Search ........................................ 204/78

[56] References Cited

U.S. PATENT DOCUMENTS 4,482,439 11/1984 Toomey ............................. 204/78

Primary Examiner—R. L. Andrews

Attorney, Agent, or Firm—Cushman, Darby & Cushman

[57] ABSTRACT

The invention relates to a process for the electrochemical oxidation of an alkylpyridine having the formula

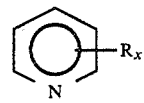

where R represents an alkyl group with 1-6 C atoms, and x is 1,2 or 3, in an acid medium at a lead-containing anode of an electrolytic cell with anode and cathode compartments separated by an ion-exchange membrane, this process being characterized in that as an ion-exchange membrane an anion-exchange membrane is used and as catholyte an aqueous solution of the same acid as used in the anolyte, which solution is dilute in respect of this anolyte, and subsequently the reaction product is recovered from the anolyte.

7 Claims, 1 Drawing Figure

PROCESS FOR THE ELECTROCHEMICAL OXIDATION OF ALKYLPYRIDINES

FIELD OF THE INVENTION

The invention relates to a process for the electrochemical oxidation of an alkylpyridine having the formula

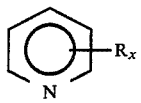

where R represents an alkyl group or a partially oxidized alkyl group with 1-6 C atoms, and x is 1, 2 or 3, in an acid medium at a lead-containing anode of an electrolytic cell with anode and cathode compartments separated by an ion-exchange membrane.

BACKGROUND OF THE INVENTION

Such a process for preparing acids of pyridine bases is known from U.S. Pat. No. 4,482,439. Such acids are valuable as intermediate products for, for instance, corrosion inhibitors, crop protection chemicals and pharmaceutical products. In the specification of that patent it is said, in column 4, lines 51-54, that both cation and anion-exchange membranes can be used, depending on the particular reaction conditions. Reference is made to the examples. In these (20) examples it is always the combination of cation-exchange membrane with acid catholyte or anion-exchange membrane with alkaline catholyte that is used. These combinations have been realized in agreement with the doctrine of Dr. F. Beck as described in his book Elektroorganische Chemie, Grundlagen und Anwendungen, Verlag Chemie (1974). On pages 112-115 of this book it is said that in an electrochemical process carried out in a continuously operating, divided electrolytic cell stationary conditions are to be expected only if in case a cation-exchange membrane is used, the anolyte is acidified, or, in case an anion-exchange membrane is used, the catholyte is alkalized. Only then are the $H^+$ ions or $OH^-$ ions transferred via the membrane to the other electrode compartment and used up at the counterelectrode to the same degree as they are injected into the first electrode compartment.

In the process as described in the opening lines the chosen anolyte will be acid, because otherwise the alkylpyridines will not be soluble in an aqueous medium. According to the above-mentioned work by Beck, in a divided electrolytic cell the chosen membrane must then be a cation-exchange membrane. A disadvantage of the process described above is that permeation of the protonated alkylpyridine may occur through the membrane from the acid anolyte to the catholyte, upon which this alkylpyridine will subsequently be hydrogenated at the cathode to form the corresponding piperidine derivative. In such a situation there will not only be a loss of raw material, but in many cases also a serious contamination of the cathode will appear.

If the process according to the opening lines is carried out in the presence of an anion-exchange membrane, an alkaline catholyte will be chosen according to Beck. With such a combination of an acid anolyte and an alkaline catholyte it is particularly the situation without any current passing through the cell that may result in an undesired reaction at the membrane (whether anion or cation-exchange) between acid and base. The heat that occurs in such a reaction is apt to result in severe damage of the membrane, particularly if concentrated solutions are used. Moreover, in consequence of diffusion, neutralization occurs also in a current-carrying state, so that acid and base are used up and contamination of the anolyte takes place in consequence of salt formation.

DESCRIPTION OF THE INVENTION

Surprisingly and contrary to the prevailing doctrine, applicant has now found that, if a process as described in the opening lines is carried out, the above-mentioned disadvantages can be overcome by the choice of an anion-exchange membrane in combination with an acid catholyte without the stationary conditions mentioned by Beck being essentially affected.

The process for the electrochemical oxidation of an alkylpyridine having the formula

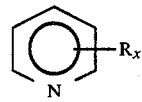

where R represents an alkyl group or a partially oxidized alkyl group with 1-6 C atoms, and x is 1, 2 or 3, in an acid medium at a lead-containing anode of an electrolytic cell with anode and cathode compartments separated by an ion-exchange membrane, is characterized in that as ion-exchange membrane an anion-exchange membrane is used and as catholyte an aqueous solution of the same acid as used in the anolyte, which solution is dilute in respect of the anolyte, and subsequently the reaction product is recovered from the anolyte.

The chosen alkyl group may in principle be a multitude of alkyl compounds, for instance those described in U.S. Pat. No. 4482439. The chosen concentration of the starting material may be in the range of 1-20% (wt).

In the process according to the invention the alkyl group or alkyl groups are oxidized to form the corresponding carboxyl group(s). A number of possible starting materials with the corresponding reaction products are shown below in Table 1:

TABLE 1

| Alkylpyridine | Pyridine acid |
| --- | --- |
| α-picoline | picolinic acid |
| β-picoline | nicotinic acid |
| 2,3-lutidine | 2,3-pyridinedicarboxylic acid |
| 2,6-lutidine | 2,6-pyridinedicarboxylic acid |
| 2-ethyl-5-methylpyridine | 2,5-pyridinedicarboxylic acid |

In case the chosen starting material is an alkylpyridine with 2 or 3 alkyl groups, it is possible also to obtain a reaction product in which, respectively, 1 or 2 carboxyl groups have been formed.

In the process according to the invention partially oxidized alkyl group is understood to mean for instance an alcohol group or aldehyde group.

The process according to the invention has a number of advantages. On the one hand, it prevents protonated alkylpyridine from finding its way into the catholyte and prevents the membrane from being badly affected and salt from being formed in the anolyte, on the other hand it is unexpectedly found that the cell voltage requirement is considerably lower than in the case in which an anion-exchange membrane is used in combination with an alkalized catholyte. Moreover, despite the allegation by Beck, virtually stationary conditions are reached. Another advantage is that anolyte and catholyte contain the same acid and no substances alien to the process are introduced into the system.

The process according to the invention is applied in an acid medium, both in the anolyte and in the catholyte. The acid must be inert. The anolyte must contain at least such an amount of acid that the alkylpyridine, whether or not partially oxidized, dissolves and sufficient conductivity is obtained. Sulphuric acid is eminently suited for acid. The anolyte contains preferably 10–50% (wt) sulphuric acid. The chosen concentration of the acid in the catholyte is lower than the free acid concentration in the anolyte and is preferably 0.1–5% (wt). Relatively speaking, the catholyte therefore contains more bisulphate ions than the anolyte.

The anion-exchange membrane is preferably a non-porous membrane, because such a membrane impedes diffusion of non-ionized molecules. Further preference is given to the use of membranes showing a high degree of selectivity for the transfer of monovalent anions, in preference to the transfer of polyvalent ions, because this results in a minimum net transfer of sulphuric acid from catholyte to anolyte.

Yet, in principle, owing to the migration of acid from the catholyte to the anolyte, the acidity in these electrolytes decreases and increases, respectively. The migration, however, is surprisingly low and constitutes only a fraction of the amount that would be expected on the basis of the transfer of current. To the person skilled in the art a number of known means are available in themselves to keep the increased acid concentration in the anolyte at its desired level. For instance, a base can be added which, together with the acid, forms an insoluble salt, and the acid in the catholyte can then be replenished. In addition to the transfer of acid, there is also a net transfer of water from catholyte to anolyte as a result of (electro)osmosis. This can be regulated by simple means. For instance, evaporation and return of the condensate to the catholyte may be considered.

The temperature at which the electrolysis can be carried out is determined mainly, in so far as its upper limit is concerned, by the stability of the membrane and, in so far as its lower limit is concerned, by the solubility of the (partially oxidized) alkypyridine and by the conductivity of the electrolytes. A systematic examination will enable the person skilled in the art to simply determine at what temperature optimum reaction efficiency is reached. Generally a temperature between 20°–90° C. is chosen.

In principle, any type of electrolytic cell is eligible for the reaction to be carried out in it. Preference, however, is given to cells of the so-called filter press type, because the membranes can be incorporated in such cells very conveniently.

The current density that can be applied is, in general, 100–5000 A.m$^{-2}$.

In the process according to the invention a certain amount of anolyte in which the alkylpyridine has been dissolved may be started from. The electrolysis may then be allowed to take place for such a length of time that almost all alkylpyridine is converted. After draining the anolyte from the electrolytic cell the reaction product can subsequently be recovered from the reaction mixture (anolyte) in a manner known per se.

Known methods are, for instance, precipitation, crystallisation and extraction.

In some cases, an additional problem can occur in the electrochemical oxidation of various pyridine bases to pyridine carboxylic acids. The fact is that if such a starting material (pyridine base) and also reaction product (pyridine carboxylic acid) are contained in the anode compartment, this reaction product will be oxidised in preference to the starting material if the concentration of the reaction product is higher than, for instance, 5% (wt). Therefore, the concentration of the reaction product in the anolyte will have to be kept low, for instance by continuously removing it. A further problem then concerns the further processing of the mother liquor, which contains valuable starting material, intermediate product and end product. If the mother liquor is returned to the anode compartment and also the catolyte is kept in circulation, the next problem arising is that owing to the migration of acid from the catholyte the acidity in the anolyte increases and the acidity in the catholyte decreases. In addition to the transfer of acid there is a net transfer of water from catholyte to anolyte as a result of (electro)osmosis.

For these cases, applicant has developed an elegant preferred embodiment of the invention, which solves the above-mentioned problems connected with electrochemical oxidation of alkylpyridines. That is, both the catholyte and the anolyte are kept in circulation, the anolyte in the circuit being dialyzed against the catholyte with continuous separation of reaction product from the anolyte and with removal of water from the anolyte and addition of water to the catholyte.

The process according to the invention is particularly suitable for the conversion of alkylpyridines, the end products of which are oxidized under the reaction conditions in preference to these alkylpyridines themselves already in low concentrations, for instance above 5% (wt). Suitable alkylpyridines are, for instance, alpha-picoline, beta-picoline, 2,3-lutidine, 2,6-lutidine and 2-ethyl-5-methylpyridine.

In the above-described embodiment of the invention acid is removed from the anolyte by dialysis with the de-acidified catholyte. A correct choice of the size of the dialyzing membrane and of the other conditions of the dialysis such as, for instance, temperature and flow rate of the liquid, will make it possible for the acid to be kept in circulation in full in a simple manner. The dialyzing membrane may be similar to the anion-exchange membrane used in the electrolysis. It is noted that in the dialyzing process, just as in the electrolyzing process, water is transferred from catholyte to anolyte by osmosis. Therefore, to the catholyte water must be supplied continuously to replenish the water transferred as a result of the osmosis. In the anolyte circuit an excess of water must be removed, for which purpose, for instance, an evaporator is present. As in this continuous process there is also a continuous withdrawal of reaction product from the anolyte, for instance by precipitation, crystallization or extraction, it will suffice to add a sufficient amount of alkylpyridine to keep the process going (in addition to the said replenishment or withdrawal of water).

This continuous process for the electrochemical oxidation of alkylpyridines is particularly suitable for application on an industrial scale.

By means of the following examples and comparative examples the invention will be further elucidated.

If not stated otherwise, the experiments were carried out in an electrolytic cell with anode and cathode placed parallel to each other, each of which consisted of a lead plate measuring 4×4 cm. The two electrodes were situated at a distance of about 2 mm from a membrane dividing the electrolytic cell into an anode and a cathode compartment. The exposed part of the membrane fitted in the cell structure was also 4×4 cm. Anolyte and catholyte were made to flow through, respectively, the anode and cathode compartments independently of each other and were kept in circulation. The chosen rate of circulation was such that the contents of the anode compartment and the cathode compartment were renewed about 500 times per hour.

The anolyte and catholyte circuits were provided with draining points and with points where extra acid, base or water could be added. The gases produced were separated off. The composition of anolyte and catholyte was determined by means of liquid chromatography as far as the organic components were concerned. The acid or base content was determined by potentiometric titration. The temperature at which the experiments were performed was 60° C. The current density was 1000 $A.m^{-2}$.

The net water transfer through the membrane was determined by level measurement.

EXAMPLE I

Composition

Anolyte: 20% (wt) sulphuric acid, 10% (wt) α-picoline, 70% (wt) water;
catholyte: 5% (wt) sulphuric acid, 95% (wt) water;
membrane: anion-exchange membrane, Selemion AMV from Asahi Glass.

During the experiment the α-picoline in the anolyte was replenished by continuously pumping in about 0.3 g α-picoline.$hour^{-1}$. After current had been passed through for 24 hours, the experiment was discontinued and the composition of anolyte and catolyte was determined.

The concentration of α-picoline in the catholyte was found to be below the detection limit of 0.05% (wt). The catholyte was virtually colourless, the cathode surface did not contain any organic deposits. The transfer of sulphuric acid from catholyte to anolyte through the membrane was 5.7 moles.$m^{-2}$.$hour^{-1}$ (determined by measuring the sulphate concentration in anolyte and catholyte before and after the electrolysis). If the transfer of charge had been effected by bisulphate ions, the expected sulphuric acid transfer would have been about 37 moles.$m^{-2}$.$hour^{-1}$ on the grounds of:

$$\frac{\text{current density } (A \cdot m^{-2}) \cdot 3600}{\text{charge of 1 mole bisulphate ions } (C \cdot mole^{-1})}$$

The cell voltage was 3.8 volts.

COMPARATIVE EXAMPLE 1

Example 1 was repeated, but this time with a catholyte composition of 5% (wt) sodium hydroxide and 95% (wt) water. Again no transfer of α-picoline through the membrane could be demonstrated. Transfer of sulphuric acid to the catholyte was found to have occurred (0.11 mole.$m^{-2}$.$hour^{-1}$) and sodium ions were present in the anolyte. Both sulphuric acid and sodium hydroxide were consumed and the anolyte was contaminated with foreign ($Na^+$) cations. The absolute magnitude of these ion transfers was smaller than in example I, as was to be expected according to Beck.

The cell voltage, however, was 4.2 volts and, moreover, after 24 hours the membrane showed a strong discolouration, which is indicative of the membrane material having been affected. (In experiments of a longer duration the membranes would break already after a few days).

COMPARATIVE EXAMPLE 2

Comparative example 1 was repeated, but this time a cation-exchange membrane (Selemion CMV from Asahi Glass) was used. Already after a few minutes the catholyte was found to produce a strong smell of α-picoline, which is indicative of undesired transfer of α-picoline.

EXAMPLE II

Composition:

Anolyte: 20% (wt) sulphuric acid, 10% (wt) 2,3-lutidine and 70% (wt) water;
catholyte: 5% (wt) sulphuric acid and 95% (wt) water;
membrane: anion-exchange membrane Selemion ASV from Asahi Glass.

For the duration of the electrolysis (69 hours) the 2,3-lutidine in the anolyte was replenished by continuously pumping in 2,3 lutidine (about 0.5 g.$hour^{-1}$). The extra volume of the anolyte (by water and sulphuric acid transfer from the catholyte) was met by a drain to a receiving vessel. Acid and water were replenished in the catholyte.

At the end of the electrolysis the catholyte was found to be colourless and the efficiency of the conversion of 2,3-lutidine into the corresponding carboxylic acids was 60% (on a molar basis) with a conversion of 68% of the total amount of 2,3-lutidine presented. The current efficiency for the conversion into carboxylic acid was 42%. The cell voltage was 3.8 volts.

COMPARATIVE EXAMPLE 3

Example II was repeated, but this time with a cation-exchange membrane, Nafion 233 from Dupont de Nemours. The experiment had to be discontinued after 51 hours. The catholyte was found to show a strong discolouration and the cathode was covered with a brown tar-like layer. The discolouration of the catholyte had been caused by 2,3-lutidine. The conversion efficiency of 2,3-lutidine into the corresponding carboxylic acids was 19.5%, while 82% of the total amount of 2,3-lutidine supplied was found to be converted. The current efficiency for the conversion into carboxylic acid was 17%.

The use of another cation-exchange membrane, Selemion CMV from Asahi Glass, produced a comparable result. Again a transfer of 2,3-lutidine through the membrane to the catholyte occurred.

EXAMPLE III

Example II was repeated and continued for 5 days, but this time using phosphoric acid instead of sulphuric acid in anolyte and catholyte. In this case the anion-exchange membrane was Selemion AMV. In this experiment, too, conversion of 2,3-lutidine into the corresponding carboxylic acids took place with an efficiency of about 60% (molar basis) in a comparable conversion. The cell voltage was 3.9 volts.

In the continuous experiments the catholyte circuit was provided with a point where water could be added. The anolyte circuit was provided with an evaporator. Anolyte and catholyte were passed through, respectively, the dilution and concentration compartments of a dialyser. The dialyzing membrane had an exposed surface eight times as large as that of the membrane in the electrolytic cell. The gases produced were separated off. The composition of anolyte and catholyte was determined by means of liquid chromatography as far as the organic components were concerned. The acid content was determined by potentiometric titration. The temperature at which the experiments were carried out was 60° C. The current density was 1000 A.m$^{-2}$. The net water transfer through the membrane was determined by level measurement.

EXAMPLE IV

Composition

Anolyte: 20% (wt) sulphuric acid, 10% (wt) 2,3-lutidine and 70% (wt) water;

catholyte: 5% (wt) sulphuric acid and 95% (wt) water;

electrolysis membrane: anion-exchange membrane, Selemion ASV from Asahi Glass;

dialyzing membrane: anion-exchange membrane, Selemion ASV from Asahi Glass.

The converted 2,3-lutidine in the anolyte was replenished by continuously pumping in 2,3-lutidine (approx. 0.15 g.hour$^{-1}$). The reaction product 2,3-pyridinedicarboxylic acid (PDC) was removed from the anolyte continuously by crystallization, while the volume of the anolyte was kept constant by evaporation. To the catholyte an amount of water was added continuously, equalling the amount removed from the anolyte.

For a period of 7 days the sulphuric acid concentration in both anolyte and catholyte remained unchanged. The concentration of pyridine bases in the catholyte continued to be below 0.1% (wt).

The composition of the anolyte, as well as of the mother liquor returned, became constant after a few hours. (Table 1).

TABLE 1

|  | anolyte | mother liquor |
| --- | --- | --- |
| 2,3-lutidine % (wt) | 10 | 10 |
| monocarboxylic acids % (wt) | 5 | 5 |
| PDC % (wt) | 2 | 1 |
| sulphuric acid % (wt) | 20 | 20 |

EXAMPLE V

In a series of experiments the current-voltage curves were measured of a number of sulphuric acid solutions with different amounts of 2,3-lutidine, 2,3-pyridinedicarboxylic acid, methylnicotinic acid and methylpycolinic acid dissolved therein. The experiments were carried out in an electrolytic cell consisting of a cylindrical lead anode and a concentric cylindrical cathode of platinum foil in which the anolyte and catholyte were kept in circulation. The anode potential was measured in respect of a saturated calomel electrode placed close to the anode by means of a glass capillary, a so-called Luggin capillary. The solution always contained 20% (wt) sulphuric acid and 0-10% (wt) 2,3-lutidine, 0-10% (wt) 2,3-pyridinedicarboxylic acid and 0-3% (wt) methylnicotinic acid or methylpicolinic acid. The average rate of the solution between the electrodes was about 0.5 m.s$^{-1}$. The current-voltage curves were measured by varying the anode potential by means of a potentiostat and recording the corresponding current through the anode. The current used for the oxidation of the pyridine bases was determined by deducting from the current measured the current passing, at the same anode potential, through a solution without pyridine bases. Subsequently, from the resulting current-voltage curves the current passing through the anode was plotted at a number of values of the anode potential against the 2,3-pyridinedicarboxylic acid content in % (wt) in a solution without 2,3-lutidine (see FIG. 1, curve 1). This was repeated for solutions with 1-10% (wt), 2,3-lutidine (see for instance FIG. 1, curve 2, for 5% (wt) 2,3-lutidine). Curve 1 in FIG. 1 gives i(PDC), the oxidation current of 2,3-pyridinedicarboxylic acid. The difference between curves 2 and 1 gives i(LUT), the oxidation current of 2,3-lutidine.

As in the oxidation of 1 molecule 2,3-lutidine to 2,3-pyridinedicarboxylic acid 12 electrons are used, and 25 electrons in the oxidation of 1 molecule 2,3-pyridinedicarboxylic acid to carbon dioxide, water and nitrogen, the selectivity of the oxidation of 2,3-lutidine to 2,3-pyridinedicarboxylic acid can be calculated as $1 - i(PDC)/i(LUT) \times 12/25$.

Of course, curves similar to those shown in FIG. 1 can be plotted for other concentrations of 2,3-lutidine. Then, from the formula described above it is possible to calculate the selectivity of the oxidation to PDC. It has been found that this selectivity is strongly influenced by the PDC concentration and that the best results as far as the selectivity is concerned are achieved with low PDC concentrations.

We claim:

1. Process for the electrochemical oxidation of an alkylpyridine having the formula

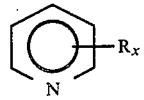

where R represents an alkyl group with 1-6 C atoms, and x is 1, 2 or 3, in an acid medium at a lead-containing anode of an electrolytic cell with anode and cathode compartments separated by an ion-exchange membrane, the process being characterized in that as ion-exchange membrane an anion-exchange membrane is used and as catholyte an aqueous solution of the same acid as used in the anolyte, which solution is dilute in respect of this anolyte, and subsequently the reaction product is recovered from the anolyte.

2. Process according to claim 1, characterized in that the acid used is sulphuric acid.

3. Process according to claim 1, characterized in that the anolyte contains 10-50% (wt) sulphuric acid and the catholyte 0.1-5 % (wt) sulphuric acid.

4. Process according to claim 1, characterized in that the anion-exchange membrane is a non-porous membrane.

5. Process according to claim 1, characterized in that the chosen membrane has a high degree of selectivity for the transfer of monovalent anions.

6. Process according to claim 1, characterized in that alkylpyridine used is α-picoline, β-picoline, 2,3-lutidine, 2,6-lutidine or 2-ethyl-5-methylpyridine.

7. The process according to claim 1, wherein said process further comprises: keeping both the anolyte and the catholyte in circulation, and further wherein the anolyte is dialyzed in the circuit against the catholyte, with continuous separation of reaction product from the anaolyte and with removal of water from the anolyte and addition of water to the catholyte.

* * * * *